United States Patent [19]

Martin et al.

[11] Patent Number: 4,573,796
[45] Date of Patent: Mar. 4, 1986

[54] APPARATUS FOR ELIMINATING BACKGROUND INTERFERENCE IN FLUORESCENCE MEASUREMENTS

[75] Inventors: John C. Martin; James H. Jett, both of Los Alamos, N. Mex.

[73] Assignee: The United States of America as represented by the United States Department of Energy, Washington, D.C.

[21] Appl. No.: 568,768

[22] Filed: Jan. 6, 1984

[51] Int. Cl.⁴ .......................... G01J 3/42; G01N 21/64
[52] U.S. Cl. ................................ 356/318; 250/461.2; 356/39; 356/73; 356/343
[58] Field of Search .................. 356/318, 317, 73, 39, 356/417, 343; 250/458.1, 459.1, 461.1, 461.2

[56] References Cited

U.S. PATENT DOCUMENTS

| | | | |
|---|---|---|---|
| 3,826,364 | 7/1974 | Bonner et al. | 356/73 X |
| 3,918,812 | 11/1975 | Holm | 250/459.1 X |
| 4,006,360 | 2/1977 | Mueller | 250/461.2 |
| 4,038,556 | 7/1977 | Auer et al. | 356/73 X |
| 4,100,416 | 7/1978 | Hirshfeld | 356/39 X |
| 4,198,567 | 4/1980 | Eneroth et al. | 250/459 |
| 4,243,318 | 1/1981 | Stohr | 356/39 |
| 4,415,265 | 11/1983 | Campillo et al. | 356/318 X |

OTHER PUBLICATIONS

Hipps, K. W. and G. A. Crosby, "Applications of the Photoelastic Modulator to Polarization Spectroscopy", The Journal of Physical Chemistry, vol. 83, No. 5, Mar. 8, 1979, pp. 555-562.

Steinkamp, Orlicky and Crissman, "Dual-Laser Flow Cytometry of Single Mammalian Cells", Jour. Histochem. Cytochem. 27, 273 (1979).

Steinkamp, Fulwyler, Coulter, Hiebert, Horney and Mullaney, "A New Multiparameter Separator for Microscopic Particles and Biological Cells", Rev. Sci. Instrum. 44, 1301 (1973).

Steinkamp, Stewart and Crissman, "Three-Color Fluorescence Measurements on Single Cells Excited at Three Laser Wavelengths", Cytometry 2, 226 (1982).

Primary Examiner—Vincent P. McGraw
Assistant Examiner—Robert D. V. Thompson, III
Attorney, Agent, or Firm—Lee W. Huffman; Paul D. Gaetjens; Judson R. Hightower

[57] ABSTRACT

The disclosure is directed to an apparatus for eliminating background interference during fluorescence measurements in a multiple laser flow cytometer. A biological particle stained with fluorescent dyes is excited by a laser. A fluorescence detector detects the fluorescence. The particle scatters light and a gate signal is generated and delayed until the biological particle reaches the next laser. The delayed signal turns on this next laser, which excites a different stained component of the same biological particle.

14 Claims, 8 Drawing Figures

APPARATUS FOR ELIMINATING BACKGROUND INTERFERENCE IN FLUORESCENCE MEASUREMENTS

This invention is the result of a contract with the Department of Energy (Contract No. W-7405-ENG-36).

BACKGROUND OF THE INVENTION

The invention described herein relates generally to multiple laser flow cytometry and more particularly to structures for eliminating background interference in fluorescence measurements made using a multiple laser flow cytometer.

In a multiple laser flow cytometer, biological cells are stained with fluorescent dyes and flow in liquid suspension through a flow chamber in which the cells are separated and aligned for measurement. When passing through the flow chamber the cells pass sequentially through spatially separated laser beams. Each laser beam excites a different fluorochrome (fluorescent dye) bound to a specific component of the cell. Measurements of the fluorescence from the fluorochromes provide quantitative information about the cell components to which the dye is bound. Flow cytometers can measure cellular properties such as cell size, DNA content, protein content and cell membrane permeability. They can also measure cellular antigens and the shape, size and deoxyribonucleic acid (DNA) content of individual chromosomes.

Multiple laser flow cytometry is described in a number of articles. J. A. Steinkamp, D. A. Orlicky, H. A. Crissman, "Dual-Laser Flow Cytometry of Single Mammalian Cells," J. Histochem. Cytochem. 27, 273 (1979). J. A. Steinkamp, C. C. Stewart, H. A. Crissman, "Three-Color Fluorescence Measurements on Single Cells Excited at Three Laser Wavelengths," Cytometry 2, 226 (1982).

Multiple laser flow cytometry has led to improved measurement capabilities for analyzing cells stained with multiple fluorochromes. Single laser excitation of cells stained with two fluorochromes requires a selection of dye combinations such that both dyes can be simultaneously excited at one laser wavelength and have minimum spectral overlap of fluorescence emission. These spectral problems have been greatly reduced by the development of dual laser flow cytometry, in which two independent laser beams intersect the flowing sample stream at different locations along the stream. This technique works well for fluorescent stains that have markedly different excitation wavelengths, although the emission spectra may completely overlap. The key to this technique is in the spatial and temporal resolution of the measurements from the separated laser beams.

Multiple laser flow cytometry works well so long as the fluorescence signals from the cells are reasonably bright and the fluorescence intensities in each measurement channel are approximately equal. However, in the case of cells where one of the measurement channels is detecting very dim fluorescence, such as immunofluorescence, there is significant background in the dim channel due to stray laser light leakage from the brighter channel laser beam. Frequently the wavelength of the other laser beam overlaps with the dim fluorescence emission spectrum and thus contributes a readily detected background. Laser blocking filters can reduce this laser leakage but they simultaneously reduce the desired dim signal. Laser leakage interference is a particularly difficult problem in dual laser measurements of chromosomes. The fluorescence from stained chromosomes is dim and in some cases the fluorescence from smaller chromosomes is so dim that photon counting statistics become important. In dual laser chromosome analysis cross interference from both laser beams can become important.

The use of laser blocking filters to reduce laser leakage is well known, but it does not solve the problem of detecting dim fluorescence in a multiple laser flow cytometer. U.S. Pat. No. 4,198,567 to Eneroth et al. discloses a method and apparatus for measuring small amounts of a fluorescent substance. The sample is excited with a radiation pulse and a fluorescence radiation detector output signal is gated so that detection of the fluorescence is delayed until after the excitation radiation pulse has decayed to a point where the fluorescence emission signal is distinctly larger than the scattered radiation signal. Eneroth et al. does not involve a multiple laser flow cytometer.

U.S. Pat. No. 4,243,318 to Stoöhr discloses a method for evaluating only the fluorescent pulses which correspond to the travel time of individual stained biological particles between the two points intersected by two laser beams. The problem addressed by Stöhr was the need to use different fluorescent dyes for DNA and protein.

SUMMARY OF THE INVENTION

One object of the present invention is to provide an apparatus which eliminates the background due to cross interference from lasers in a multiple laser flow cytometer.

Another object of the invention is to provide an apparatus for controlled turning on and off of laser beams in a multiple laser flow cytometer.

Still another object of the invention is to detect dim fluorescence.

Another object of the invention is to make precise fluorescence measurements of chromosomes.

To achieve the foregoing and other objects, and in accordance with the purposes of the present invention, as embodied and broadly described herein, there is provided in a multiple light source flow cytometer the improvement consisting of an apparatus for modulating on and off light from at least one light source to eliminate background interference between the light sources of the flow cytometer. The flow cytometer, which forms no part of the present invention, includes at least first and second light sources, which are typically lasers. The lasers may emit light having the same wavelength or different wavelengths. The laser beams are focused and intersect the path of biological particles at different points. Each laser ordinarily excites a different fluorescent dye bound to a specific component of a biological particle. The cytometer includes at least one fluorescence detector to measure the fluorescence from the dyes, and a data storage system for storing fluorescence data.

The apparatus in accordance with the present invention comprises first and second light scatter detectors for detecting light scattered by biological particles, first and second gate signal generators responsive to the respective light scatter detectors, and first and second gated signal processors for receiving first and second gate signals from the respective gate signal generators and for transmitting fluorescence data to the data storage system. The apparatus further includes at least one optical modulator which modulates one of the light sources on and off. A delay device is connected to and receives a gate signal from a gate signal generator and generates a delayed gate signal in response thereto. The delay device is connected to the optical modulator such that the delayed gate signal controls the operation of the optical modulator. The optical modulator may be associated with either the first light source or the second light source. Preferably a first optical modulator is associated with the first light source and a second optical modulator is associated with the second light source. The biological particles may be chromosomes. Where the biological particles are sufficiently small that light of sufficient strength to be detected is not scattered, the gate signal generators can be responsive to the respective fluorescence detectors.

One advantage of the present invention is that the background due to cross interference from light sources in a multiple light source flow cytometer is eliminated.

Another advantage of the invention is that dim florescence can be detected.

Still another advantage of the invention is that precise fluorescence measurements of chromosomes using multiple lasers can be obtained.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings:

FIG. 6 graphically illustrates fluorescence data obtained with a dual laser flow cytometer in which both lasers were always on.

DETAILED DESCRIPTION OF THE INVENTION

Figure 1:
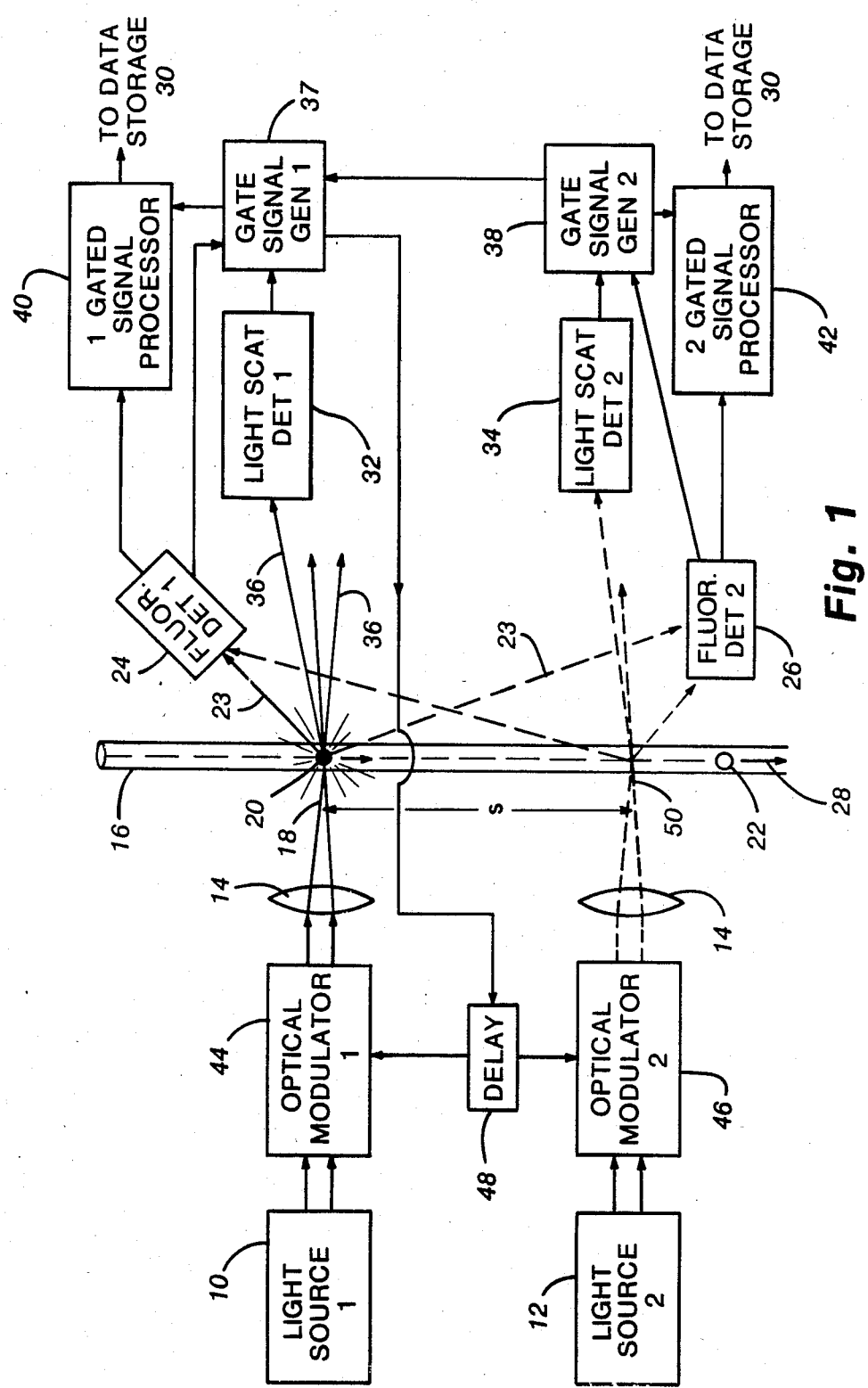
FIG. 1 shows a schematic view of a preferred embodiment of the invention.

Reference is now made to FIG. 1 which shows a schematic view of a preferred embodiment of the invention. The apparatus of the present invention is shown in combination with portions of a flow cytometer. The flow cytometer includes a first light source 10 and a second light source 12. The flow cytometer also includes focusing optics 14 to focus the light from each light source onto different points separated by a distance S along the sample stream 16 through which biological particles pass in single file, much like beads spaced apart on a string. The light sources may be lasers which emit light having different wavelengths or the same wavelength. The laser can be pulsed or continuous wave (cw). First light beam 18 from first light source 10 is showing exciting first biological particle 20. First biological particle 20 and second biological particle 22 are stained without fluorescent dyes. Each dye is bound to a specific component of a biological particle. Each light source can excite the same or a different dye. The first biological particle 20 is shown giving off fluorescence 23 which is detected by first fluorescence detector 24. Light from light beam 18, as well as fluorescence 23, reaches second fluorescence detector 26. The direction of movement of the biological particles is indicated by arrow 28. The flow cytometer also includes a data storage system 30 for storing fluorescence, light scatter and other data obtained about the biological particles.

The apparatus in accordance with the present invention modulates on and off at least one light source to eliminate background interference during fluorescence measurements. The apparatus includes a first light scatter detector 32 and a second light scatter detector 34. First biological particle 20 is shown giving off scattered light 36. First gate signal generator 37 generates a first gate signal in response to the detection of scattered light by first light scatter detector 32. Second gate signal generator 38 generates a second gate signal in response to the detection of scattered light by second light scatter detector 34. First gated signal processor 40 and second gated signal processor 42 receive the respective gate signals and transmit fluorescence and light scatter data to the data storage system 30. First optical modulator 44 is operably associated with first light source 10. Second optical modulator 46 is operably associated with second light source 12. First optical modulator 44 and second optical modulator 46 are connected to delay device 48. First biological particle 20 is shown giving off fluorescence 23 detected by first fluorescence detector 24 and producing scattered light 36 which reaches first light scatter detector 32. At this instant the interference signal from first light beam 18, which reaches the second fluorescence detector 26, is blocked at second gated signal processor 42. First gate signal generator 37 generates a first gate signal in response to first light scatter detector 32. The first gate signal is sent to delay device 48. First gate signal generator 37 also generates a third gate signal which is sent to first gated signal processor 40 to block the signal from the first fluorescence detector 24, so that it will not process signals when first biological particle 20 reaches second light beam 50 (shown in broken lines to indicate that second light source 12 is off). Delay device 48 immediately relays the first gate signal to first optical modulator 44 which modulates off the light from first light source 10 after first biological particle 20 has left the first light beam 18. Delay device 48 produces a delayed gate signal in response to the first gate signal. The first gate signal is, effectively, delayed for a time sufficient for first biological particle 20 to travel the distance S from the first light beam 18 to the second light beam 50. When second optical modulator 46 receives the delayed gate signal from delay device 48, it pulses second light source 12 on for a sufficiently long time period to excite first biological particle 20. Second fluorescence detector 26 detects the resultant fluorescence and second light scatter detector 34 detects scattered light. Fluorescence and light scatter data are sent to data storage 30 via second gated signal processor 42. Second gate signal generator 38 generates a fourth gate signal in response to second light scatter detector 34. The fourth gate signal is sent to first gate signal generator 37, from which it is sent to first gated signal processor 40 to turn first fluorescence detector 24 back on. It is also sent to delay device 48 and in turn to first optical modulator 44 which then modulates the light from first light source 10 back on. First light beam 18 is then able to excite the next biological particle in the sample stream 16 to reach first light beam 18. The biological particles can be cells, viruses, molecules, bacteria, or chromosomes. The light sources can be pulsed flash lamps or mercury vapor lamps. The optical modulators can be electrooptical modulators, acoustooptical modulators or liquid crystal switches.

In another embodiment of the invention, still referring to FIG. 1, there is only one optical modulator, second optical modulator 46. First light beam 18 is left on continuously. Delay device 48 and second optical modulator 46 pulse on second light source 12 for a time sufficiently long to excite the same biological particle that caused a gate signal to be generated and reach delay device 48 by scattering light from first light beam 18 or by giving off fluorescence.

In another embodiment of the invention, still referring to FIG. 1, the only optical modulator is first optical modulator 44. Second light beam 50 is left on continuously. After a biological particle scatters light from second light beam 50, a gate signal is generated and routed to first optical modulator 44 to modulate on first light beam 18. First light beam 18 is then able to excite the next biological particle in the sample stream 16.

Figure 2:
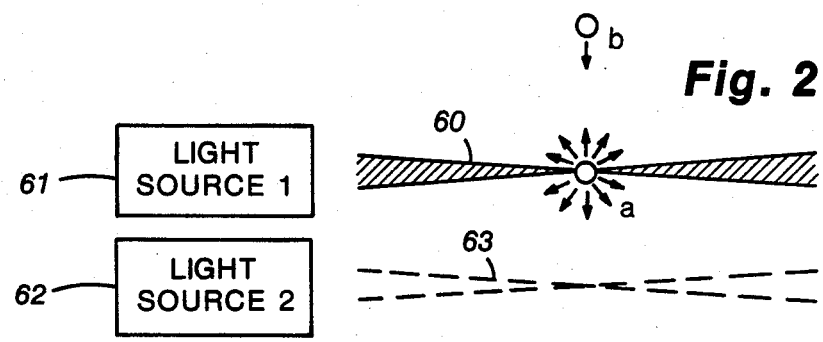
FIGS. 2, 3, 4, and 5 schematically illustrate the modulation of the light sources in the preferred embodiment of the invention.
Figure 3:
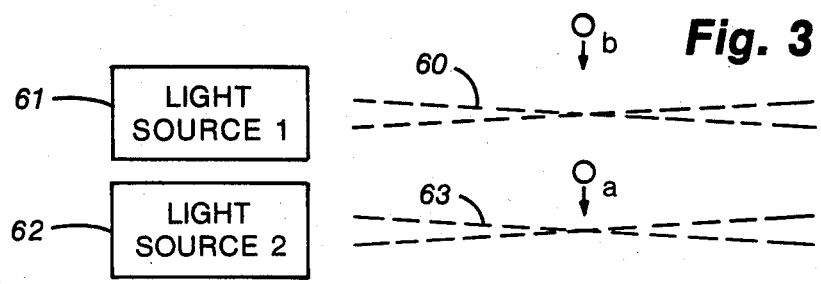
Figure 4:
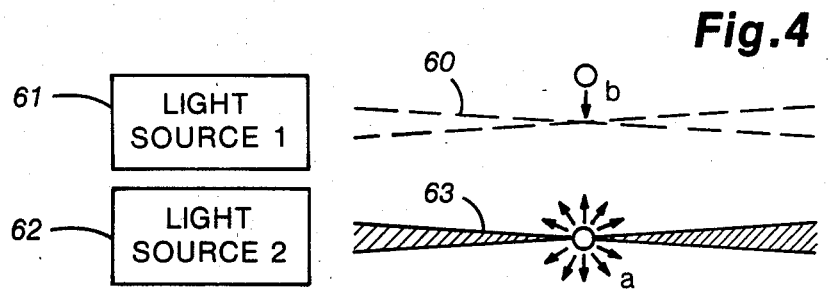
Figure 5:
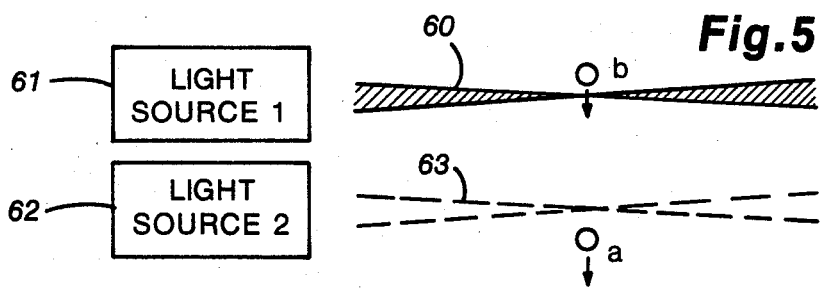

FIGS. 2, 3, 4 and 5 schematically illustrate the modulation of the light sources in the preferred embodiment of the invention shown in FIG. 1. FIG. 2 shows biological particle a as it is excited by a first light beam 60 from first light source 61. Second light source 62 is off, as is represented by the broken lines showing where second light beam 63 would be. FIG. 3 shows first light source 61 and second light source 62 off, with biological particle a between first light beam 60 and second light beam 63. FIG. 4 shows second light source 62 on and particle a being excited by second light beam 63. First light source 61 and first light beam 60 are off. FIG. 5 shows second light source 62 and second light beam 63 off. First light source 61 has been turned on. Biological particle b is shown approaching first light beam 60.

Figure 8:
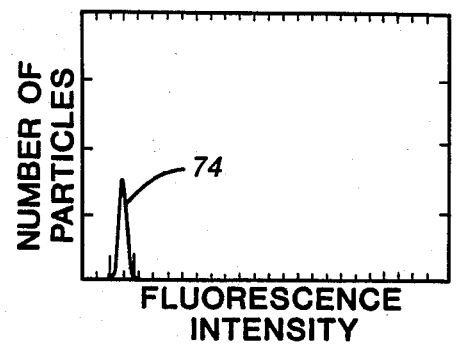
FIG. 8 graphically illustrates fluorescence data obtained with a dual laser flow cytometer in which one laser was always on and the other laser was modulated on and off.
Figure 7:
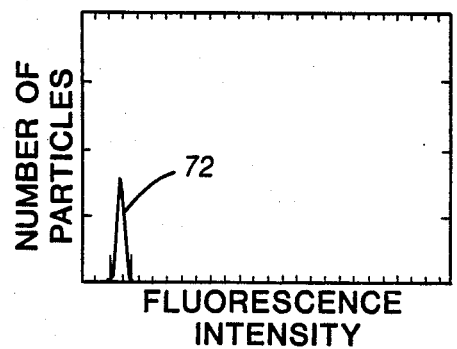
FIG. 7 graphically illustrates fluorescence data obtained with a dual laser flow cytometer in which one laser was always on and the other laser beam was blocked.
Figure 6:
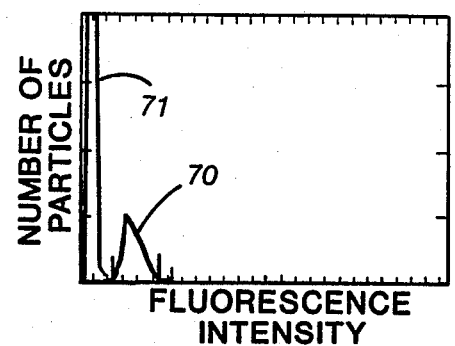

FIG. 6 graphically illustrates fluorescence data obtained with a dual laser flow cytometer in which both lasers were always on. FIG. 7 graphically illustrates fluorescence data obtained with a dual laser flow cytometer in which one laser was always on and the other (interfering) laser beam was blocked. FIG. 8 graphically illustrates fluorescence data obtained with a dual laser flow cytometer in which one laser was always on and the other laser was modulated on and off. In FIGS. 6, 7, and 8 the vertical axis corresponds to the number of particles and the horizontal axis corresponds to fluorescence intensity. A narrow peak indicates that the measurements made were precise and resolution was good. As can be seen in FIG. 6, the peak 70 obtained using a conventional dual laser flow cytometer is fairly broad and is shifted to the right because of the background contribution. In addition, there are a number of background signals 71. In FIG. 7 the peak 72 is much narrower. The peak 74 in FIG. 8 is also much narrower.

In obtaining the data represented in FIG. 8, the delay device used was an Ortec gate and delay generator, model 416A. The optical modulator was a Coherent model 317. The light sources were argon-ion lasers. The first light source was Spectra Physics Model 164-04 with a wavelength of 457.9 nm. The second light source was Spectra Physics Model 164-05 with a wavelength of 514.5 nm. The laser blocking filter used for the 457.9 nm excited fluorescence was a Schott GG495.

The foregoing description of several embodiments of the invention has been presented for purposes of illustration and description. It is not intended to be exhaustive or to limit the invention to the precise forms disclosed. They were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. In a flow cytometer measuring device having first and second light sources for forming respective first and second beams of focused light to excite different fluorescent dyes bound to specific components of biological particles, the measuring device including a fluorescence detector for producing fluorescence data, and a data storage system for storing said fluorescence data, the improvement comprising an apparatus for modulating on and off light from a light source to eliminate background interference from one light source while the other light source excites the biological particle and the resulting fluorescence is detected, said apparatus including:

a. first and second light scatter detectors for detecting light scattered by biological particles;
   b. first and second gate signal generators for generating first and second gate signals, said first gate signal generator being responsive to said first light scatter detector and said second gate signal generator being responsive to said second light scatter detector;
   c. first and second gated signal processing means for receiving said first and second gate signals respectively and for transmitting the fluorescence data to the data storage system, said first gated signal processing means being connected to said first gate signal generator, the fluorescence detector and the data storage system, said second gated signal processing means being connected to said second gate signal generator, the fluorescence detector and the data storage system;
   d. delay means for delaying said gate signal generated by one of said gate signal generators, said delay means being connected to receive said gate signal and producing a delayed gate signal in response thereto; and
   e. an optical modulator associated with one of the light sources, said optical modulator being connected to said delay means to receive said delayed gate signal and modulate on and off the light from the light source in response thereto.

2. The invention of claim 1 wherein the light sources are lasers.

3. The invention of claim 1 wherein the biological particles are chromosomes.

4. The invention of claim 1 wherein each light source emits light having the same wavelength.

5. The invention of claim 1 wherein each light source emits light having different wavelengths.

6. The invention of claim 1 wherein the flow cytometer measuring device includes first and second fluorescence detectors, said first gated signal processing means being connected to the first fluorescence detector and said second gated signal processing means being connected to the second fluorescence detector.

7. The invention of claim 1 wherein said optical modulator is associated with the second light source and wherein said delay means delays said first gate signal generated by said first gate signal generator until the biological particle has moved from the first light beam to the second light beam.

8. The invention of claim 1 wherein said optical modulator is associated with the first light source and wherein said optical modulator modulates off light from the first light source after the first light scatter detector detects a biological particle until the same biological particle is detected by the second light scatter detector.

9. The invention of claim 8 further comprising a second optical modulator, said second optical modulator being associated with the second light source and wherein said delay means delays said first gate signal generated by said first gate signal generator until the biological particle has moved from the first light beam to the second light beam.

10. In a flow cytometer measuring device having first and second light sources for forming respective first and second beams of focused light to excite different fluorescent dyes bound to specific components of sufficiently small biological particles that light of sufficient strength to be detected is not scattered, the measuring device including first and second fluorescence detectors for producing fluorescence data, and a data storage system for storing said fluorescence data, the improvement comprising an apparatus for modulating on and off light from a light source to eliminate background interference from one light source while the other light source excites the biological particle and the resulting fluorescence is detected, said apparatus including:

a. first and second gate signal generators for generating first and second gate signals, said first gate signal generator being responsive to the first fluorescence detector and said second gate signal generator being responsive to the second fluorescence detector:

b. first and second gated signal processing means for receiving said first and second gate signals respectively and for transmitting the fluorescence data to the data storage system, said first gated signal processing means being connected to said first gate signal generator, the first fluorescence detector and the data storage system, said second gated signal processing means being connected to said second gate signal generator, the second fluorescence detector and the data storage system;

c. delay means for delaying the gate signal generated by one of said gate signal generators, said delay means being connected to receive said gate signal and producing a delayed gate signal in response thereto; and d. an optical modulator associated with one of the light sources, said optical modulator being connected to said delay means to receive said delayed gate signal and modulate on and off the light from the light source in response thereto.

11. The invention of claim 10 wherein the biological particles are chromosomes.

12. The invention of claim 10 wherein the light sources are lasers.

13. The invention of claim 10 wherein each light source emits light having the same wavelength.

14. The invention of claim 10 wherein each light source emits light having different wavelengths.

* * * * *